(12) United States Patent
Tomer et al.

(10) Patent No.: US 6,274,176 B1
(45) Date of Patent: *Aug. 14, 2001

(54) HERBAL COMPOSITIONS AND THEIR USE AS ANTI-INFLAMMATORY AGENTS FOR ALLEVIATION OF ARTHRITIS AND GOUT

(75) Inventors: Onkar S. Tomer, Watchung; Peter Glomski, South Amboy; Kripanath Borah, Morris Plains, all of NJ (US)

(73) Assignee: Chromak Research, Inc., Somerset, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/346,252

(22) Filed: Jul. 1, 1999

(51) Int. Cl.$^7$ .................................................... A61K 35/78
(52) U.S. Cl. ......................... 424/725; 424/733; 424/756; 424/764
(58) Field of Search .................... 424/195.1, 725, 424/764, 756, 733

(56) References Cited

U.S. PATENT DOCUMENTS

| | | | |
|---|---|---|---|
| 4,666,701 | * | 5/1987 | Horrobin et al. . |
| 4,704,279 | * | 11/1987 | Hancock . |
| 5,120,538 | | 6/1992 | Oei . |
| 5,166,139 | * | 11/1992 | Bombardelli et al. . |
| 5,212,201 | * | 5/1993 | Wakashiro et al. . |
| 5,494,668 | | 2/1996 | Patwardhan . |
| 5,529,778 | | 6/1996 | Rohatgi . |
| 5,683,698 | | 11/1997 | Chavali et al. . |
| 5,707,631 | | 1/1998 | Lieberman . |
| 5,900,240 | | 5/1999 | Tomer et al. . |

OTHER PUBLICATIONS

Afifi et al. Vet. Med. J. Giza, vol. 42, No. 3, pp. 85–92, 1994.*
Abstract of DE 29,711,242 U1, Feb. 1998.*
Abstract of NL 8,203,249 A, Mar. 1984.*
Yesilada et al. Planta Med, vol. 56, No. 6, p. 659, 1990.*
Drug Launches database on STN: Arthroformula produced by Vitaplex, lauched 10/97, Feb. 9, 1998.*

* cited by examiner

*Primary Examiner*—Francisco Prats
*Assistant Examiner*—Susan D. Coe
(74) *Attorney, Agent, or Firm*—Jack Matalon

(57) ABSTRACT

An edible composition for use as an anti-inflammatory agent for alleviation of arthritis and gout in mammals. The edible composition is a mixture of at least three, preferably at least seven, herbs selected from the group consisting of *Tanacetum parthenium, Zingibar officinale, Curcuma longa, Coriandrum sativum, Centella asiatica, Oenothera biennis, Valeriana officinalis, Tabebuia impetiginosa, Thymus vulgaris* and *Sambucus nigra*. A preferred composition will contain at least *Tanacetum parthenium, Zingibar officinale* and *Curcuma longa*. The composition preferably contains the herbs in approximately equal amounts.

4 Claims, No Drawings

HERBAL COMPOSITIONS AND THEIR USE AS ANTI-INFLAMMATORY AGENTS FOR ALLEVIATION OF ARTHRITIS AND GOUT

FIELD OF THE INVENTION

The present invention is directed to an edible composition for use as an anti-inflammatory agent for alleviation of arthritis and gout in mammals. The composition comprises a synergistic mixture of at least three herbs selected from a group of ten herbs identified below.

BACKGROUND OF THE INVENTION

The prior art is replete with references to herbal medicines for treatment of a variety of ailments in mammals. Typically, such herbal medicines are obtained as the active compound (s) by extraction from plant tissues. Although the use of various herbs have been described in related areas, the synergistic combination of the herbs in the edible composition of the invention has never previously been described.

Japanese Patent Publication No. 4,005,237 discloses a combination of *Cinnamomum sieboldii* and *Allium sativum* for superoxide scavenging in the treatment of inflammatory disorders. German patent Publication No. 3,724,341 discloses a combination of *Cinnamomum zeylanicum, Pumica granitum* cortex, *Cardamon zingiberaceie* fruit and *Piper longum* fruit.

U.S. Pat. No. 5,494,668 is directed to a method of treating degenerative musculoskeletal diseases such as rheumatoid arthritis and osteoarthritis in an animal, typically a human, by enteric administration of a therapeutically effective amount of the beneficiated extracts of the plants *Withania somnifera, Boswellia serrata, Curcuma longa* and *Zingiber officinale* in a predetermined proportion to each other.

U.S. Pat. No. 5,120,538 is directed to a method of treating inflammation in a patient by administration of an effective dose of a pharmaceutical composition comprising essential oils extracted from tissues of *Curcuma domestica,* or *Curcuma xanthorrhiza* or both oils and curcuminoid substantially free of bis-desmethoxycurcumin.

U.S. Pat. No. 5,707,631 is directed to a therapeutic herbal composition including *Trigonella foenum-graecum* seed, *Syzygium aromaticum* fruit, *Allilum sativum* bulb, *Cinnamomum zeylanicum* bark, *Saussurea costus* root and *Euphorbia lathyris* bud together with sodium chloride (preferably sea salt).

Arthritis is a chronic syndrome characterized by inflammation of the peripheral joints, while gout manifests itself as an inflammation of the lower leg. For the sake of brevity, whenever reference hereinbelow is made to arthritis, it should be understood as encompassing gout, since the principal difference between arthritis and gout is the location of the inflamed joints. There is a wide spectrum of disease severity but many patients run a course of intermittent relapses and remissions with an overall pattern of slowly progressive joint destruction and deformity. Persistent inflammation produces symptoms and damages tissue causing loss of cartilage, erosion of bone matter and subluxation of the joint. This results in a high degree of morbidity resulting in disturbed daily life of the patient. Diagnosis of arthritis is typically carried out by determination of rheumatoid factor in the blood and radiological changes in the peripheral joints.

Present treatment of arthritis includes first line drugs for control of pain and inflammation classified as non-steroidal anti-inflammatory drugs (NSAIDs), e.g., aspirin, ibuprofen, naproxen, methotrexate, etc. Secondary treatments include corticosteroids, slow acting antirheumatic drugs (SAARDs) or disease modifying drugs (DMs), e.g., penicillinamine, cyclophosphamide, gold salts, azothipprine, levamisole, etc.

All of the foregoing drugs have a variety of toxic side effects and most of them are cytotoxic. These drugs have limited advantages and their effects are mainly of short term duration. The side effects they produce, e.g., gastric erosion, and adverse effects on the kidneys and liver, dictate against their use over extended periods of time. Further the drugs used at present are costly and have low benefit-risk ratios. There still remains a need for alternative therapies for the management of arthritis which are moderate in cost, safe, efficacious and which eliminate the need for traditional drugs and their associated side effects, particularly over prolonged daily use.

SUMMARY OF THE INVENTION

This invention describes an edible composition for use as an anti-inflammatory agent for alleviation of arthritis and gout in mammals. Since the composition comprises a mixture of herbs as described below, the composition meets all of the criteria set forth above, i.e., it is relatively inexpensive, produces no adverse side effects, may be taken in multiple daily doses over prolonged periods of time and it results in the alleviation of arthritis (and gout) in the patient within a few weeks after commencement of ingestion of the composition.

DETAILS OF THE INVENTION

The edible composition of the invention comprises a mixture of at least three herbs selected from the group consisting of the following ten herbs:

TABLE

| Stream | 200 | 220 | 217 | 213 |
| --- | --- | --- | --- | --- |
| Composition, Mol % | | | | |
| H2 | 42.50 | 47.48 | 0.00 | 0.00 |
| CO | 47.80 | 50.69 | 23.18 | 23.18 |
| CH4 | 9.40 | 1.50 | 76.77 | 76.77 |
| N2 | 0.30 | 0.33 | 0.05 | 0.05 |
| Total: | 100.00 | 100.00 | 100.00 | 100.00 |
| Flow, lb. mol/hr. | 1000.0 | 894.9 | 105.1 | 457.0 |
| Temp. ° F. | 104 | 84 | 104 | 84 |
| Pressure, psig | 363 | 350 | 140 | 5.0 |

Preferably, the mixture contains at least seven of the above-listed ten herbs. More preferably, the mixture will contain at least the following three herbs: *Tanacetum parthenium, Zingibar officinale* and *Curcuma longa.*

The ratio of the herbs in the edible composition is not critical, e.g. each herb may be present in amounts as low as 10 wt. %, based on the weight of the composition, with the balance being the other herbs. However, as a matter of convenience, it is preferable that the composition contain approximately equal amounts of each herb.

Preferably, the compositions contain no fillers or enhancing agents, since such materials are unnecessary and merely serve to dilute the effective concentration of the herbs and to decrease the absorption rate into the blood-stream after ingestion.

The individual herbs, obtained from the preferable sources indicated above, may be used in the form of extracts using aqueous and non-aqueous solvents (e.g. ethanol, isopropanol, acetone, etc., which are evaporated off prior to use). Preferably, the herbs are milled and mixed as fine, dry powders. The dry powder mix may then be further processed into the form of compressed tablets, caplets or lozenges or processed into pouches (i.e. "tea" bags) from which water infusions are ingested.

The preferable method of processing the compositions of the invention for ingestion is to package the powdered herbal mixture into gelatin capsules (preferably hard gelatin) of a size preferably of the order of zero or double zero. Such capsules would then contain about 300–600 mg of the powdered herbal mixture per capsule. It has been found that hard gelatin capsules represent the most efficient, economical form of packaging of the edible composition for ingestion.

The dosage of the herbal compositions of the invention to be ingested will vary, depending on factors such as severity of the arthritis, age, physical condition and body weight of the patient, diet, etc. As a general guide, it is expected that patients with a body weight in the range of 60–90 kg would ingest about 1,000–5,000 mg/day of the herbal compositions (corresponding to 2–12 zero or double zero size hard gelatin capsules per day). Typically, a human patient would ingest about 40 mg of the composition per kg of body weight. It is to be understood that these dosage levels are only general guides and the proper dosage level for individual patients may vary considerably depending on the factors indicated above. However, one benefit of the edible compositions of the present invention is that the dosage is not "critical" as is the case with administration of synthetic pharmaceutical medications such as those mentioned above. Since the edible compositions of the present invention are holistic in nature and represent dietary supplements in their own right, "overdosing" is not a problem. The individual patient with a particular body weight and life style may readily determine the proper dosage by starting out with the general dosage level set forth above and adjust the dosage as necessary to alleviate the arthritis.

The following non-limiting examples shall serve to illustrate the invention. Unless otherwise indicated, all amounts and parts are on a weight basis.

EXAMPLE 1

Finely milled, dry powders of *Tanacetum parthenium, Zingibar officinale, Curcuma longa, Coriandrum sativum, Centella asiatica, Oenothera biennis* and *Valeriana officinalis* were blended together in equal amounts. The resultant mixture was then used to test a strain of mice known to develop serious arthritic symptoms. The particular strain of mice used in this example is known as MRL/MPJFas<lpr>; this strain is frequently used for testing of arthritic symptoms.

The mice were divided into two groups with three mice in each group. One group was used as the control and the other group was used to test the effect of the mixture of the seven herbs indicated above. The control group ingested by demand 10–15 ml of plain water over a period of 8 weeks. The test group ingested the same volume of water which contained 450 mg/l of the mixture of the seven herbs over the same period of 8 weeks.

Blood samples were taken from the tails of each group of mice after 8 weeks and were tested for the presence of the Rheumatoid Factor ("RF"). The diagnostic kit for this test consisted of a Rheumaton Diagnostic Reagent obtained from Wampole Laboratories, a division of Carter-Wallace. The diagnostic test was carried out by mixing the serum of the blood specimen with the reagent. A visible agglutination ("positive") will indicate the presence of the RF and hence the presence of an arthritic condition. Absence of agglutination ("negative") is indicative of the absence of the RF and hence the absence of an arthritic condition.

The diagnostic test was positive for all the mice in the control group, while it was negative for all the mice in the test group. These results indicate that the composition of the invention is efficacious in preventing the onset of arthritic conditions.

EXAMPLE 2

Two human males of approximately 160 lb each served as test subjects for this example. The test subjects suffered from gout which was manifested by significant swelling of the ankles.

Since gout is somewhat seasonal in nature, i.e. the severity increases during humid seasons, the test subjects each ingested, on a daily basis, six zero sized capsules containing about 450 mg per capsule of the herbal mixture employed in Example 1 commencing a few weeks before the humid season, throughout the humid season and for a few weeks subsequent to the end of the humid season. The test subjects indicated that they felt less ankle pain within a few weeks after commencing ingestion of the capsules. Further, by the end of the humid season, it was noted that there was a significant reduction of the swelling of the ankles in each test subject.

EXAMPLE 3

In this example, 4 human males (averaging 160 lb body weight) and 2 human females (averaging 130 lb body weight) served as the test subjects. Each of the test subjects suffered from arthritis in the hands, feet and lower back. Each test subject commenced the ingestion of six zero size capsules per day, with each capsule containing about 450 mg per capsule of the herbal mixture employed in Example 1. Approximately 2 weeks after ingestion of the capsules commenced, each test subject indicated an alleviation of the arthritic conditions. After several months of ingestion of the same daily dosage of the herbal mixture, each test subject exhibited a significant reduction in the swelling of the joints of the hands and feet.

The results of Examples 2 and 3 indicated that the herbal composition of the invention is safe and is efficacious in alleviating the conditions of gout as well as arthritis.

What is claimed is:

1. An edible composition for use as an anti-inflammatory agent for alleviation of arthritis and gout in mammals comprising a mixture of at least seven herbs selected from the group consisting of *Tanacetum parthenium, Zingibar officinale, Curcuma longa, Coriandrum sativum, Centella asiatica, Oenothera biennis, Valeriana officinalis, Tabebuia impetiginosa, Thymus vulgaris* and *Sambucus nigra*.

2. The composition of claim 1 wherein each of the herbs are present in the mixture in equal amounts.

3. The composition of claim 1 comprising a mixture of *Tanacetum parthenium, Zingibar officinale, Curcuma longa, Coriandrum sativum, Centella asiatica, Oenothera biennis* and *Valeriana officinalis* blended together in approximately equal amounts.

4. The composition of claim 1 wherein each of the herbs are present in the mixture in an amount of at least 10 wt. %, based on the weight of the composition.

\* \* \* \* \*

UNITED STATES PATENT AND TRADEMARK OFFICE
CERTIFICATE OF CORRECTION

PATENT NO. : 6,274,176 B1  Page 1 of 1
DATED : August 14, 2001
INVENTOR(S) : O.S. Tomer et al.

It is certified that error appears in the above-identified patent and that said Letters Patent is hereby corrected as shown below:

Column 2,
Lines 35-49, delete in its entirety and insert instead the following:

| Botanical Name | Common Name | Preferred Source |
|---|---|---|
| *Tanacetum parthenium* | Feverfew | leaf |
| *Zingibar officinale* | Ginger | rhizome |
| *Curcuma longa* | Turmeric | rhizome |
| *Coriandrum sativum* | Cilantro/Coriander | seed |
| *Centella asiatica* | Gotu Kola | entire plant |
| *Oenothera biennis* | Evening Primrose | seed |
| *Valeriana officinalis* | Valerian | root |
| *Tabebuia impetiginosa* | Pau D' Arco | bark |
| *Thymus vulgaris* | Thyme | leaf |
| *Sambucus nigra* | Elderberry | leaf and flower |

Signed and Sealed this

Twenty-seventh Day of May, 2003

JAMES E. ROGAN
*Director of the United States Patent and Trademark Office*